United States Patent [19]
Kimber

[11] Patent Number: 5,478,321
[45] Date of Patent: Dec. 26, 1995

[54] PLASTIC SYRINGE

[76] Inventor: Michael B. Kimber, "Treetops" The Waterfront, Berowra Waters, New South Wales 2082, Australia

[21] Appl. No.: 87,785

[22] PCT Filed: Jan. 9, 1992

[86] PCT No.: PCT/AU92/00007
§ 371 Date: Jul. 14, 1993
§ 102(e) Date: Jul. 14, 1993

[87] PCT Pub. No.: WO92/12746
PCT Pub. Date: Aug. 6, 1992

[30] Foreign Application Priority Data

Jan. 15, 1991 [AU] Australia ................... PK4204

[51] Int. Cl.⁶ .................................................. A61M 5/00
[52] U.S. Cl. ..................... 604/187; 604/218; 604/232; 604/243
[58] Field of Search ..................... 604/187, 192, 604/193, 194, 195, 197, 218, 232, 233, 234, 220, 235, 236, 240, 241, 243, 244, 249, 110, 111, 228, 158, 200, 237, 238, 905; 128/763, 764

[56] References Cited

U.S. PATENT DOCUMENTS

| | | | |
|---|---|---|---|
| 3,577,980 | 5/1971 | Cohen | 128/765 |
| 3,941,128 | 3/1976 | Baldwin | 604/238 |
| 4,233,975 | 11/1980 | Yerman | |
| 5,017,191 | 5/1991 | Yamada et al. | 604/243 |
| 5,383,864 | 1/1995 | Van den Hevvel | 604/218 |

FOREIGN PATENT DOCUMENTS

| | | |
|---|---|---|
| 0347742 | 12/1989 | European Pat. Off. . |
| 6941553 | 10/1971 | France . |
| 1814466 | 1/1970 | Germany . |
| 632166 | 9/1982 | Switzerland . |

OTHER PUBLICATIONS

International Search Report.

*Primary Examiner*—C. Fred Rosenbaum
*Assistant Examiner*—L. Alexander
*Attorney, Agent, or Firm*—Vidas, Arrett & Steinkraus

[57] ABSTRACT

A prefilled disposable plastic syringe (1) comprising an open ended barrel (2) having a needle fitting (6) disposed at one end and being sealed at the other end by a moveable stopper (4) wherein said needle fitting end of the barrel (2) is sealed by a frangible closure (7) which is integral with the needle fitting (6), said closure being adapted to cooperate with a hypodermic needle support (21) shaped to fit onto said needle fitting (6) such that application of a downward force on said hypodermic needle support (21) onto said needle fitting (6) causes said closure (7) to separate from the needle fitting and move at least some way into the body of the syringe (1) and thereby reveal the contents of the syringe (1) for injection.

14 Claims, 3 Drawing Sheets

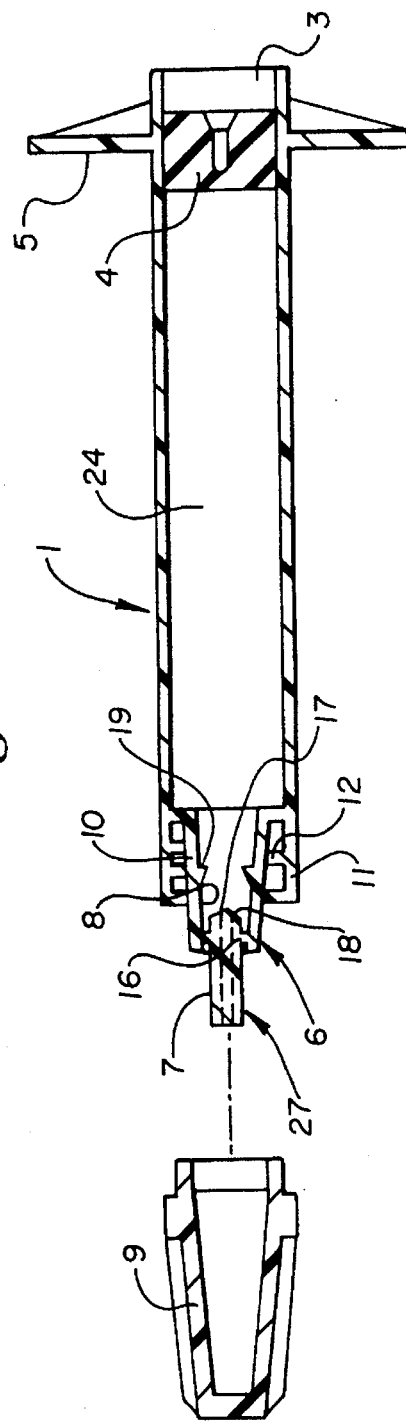
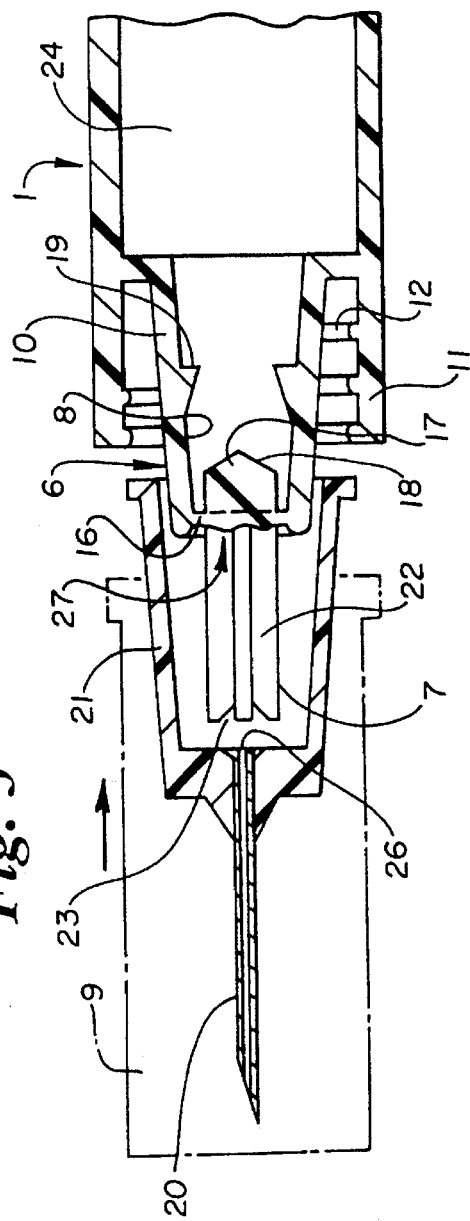
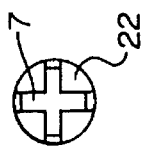

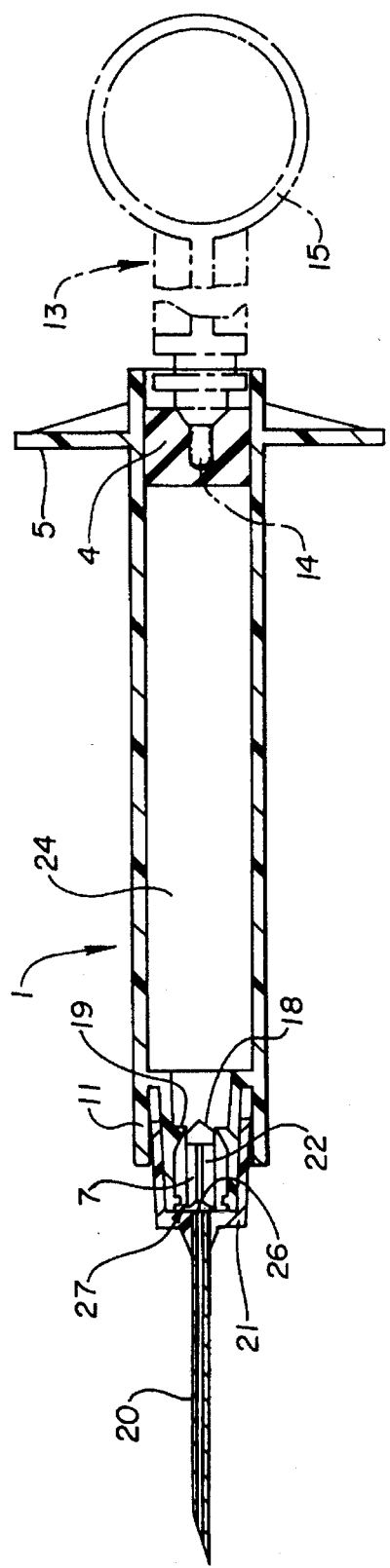
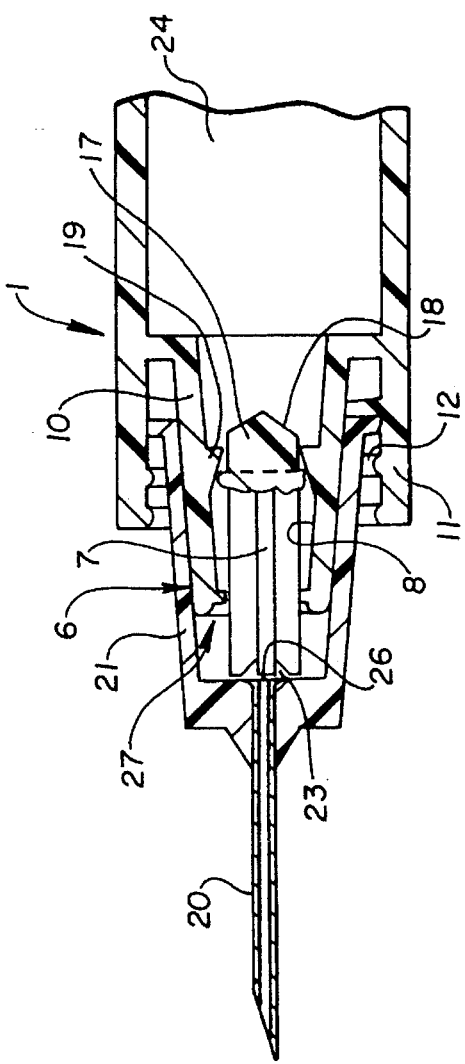

PLASTIC SYRINGE

BACKGROUND OF THE INVENTION

This invention relates to a disposable syringe intended for single use.

Since use disposable syringes for medical purposes are well known and are in everyday use. Such syringes are more convenient than re-usable syringes as there is no need for the medical practioner to maintain sterilising facilities for the various components used with re-usable syringes. A disposable syringe can be prepackaged in a sterile condition and thus be available for use immediately when required. This makes such syringes particularly useful when administration of any particular injectable is required in emergency situations.

With respect to particular injectable solutions, it is often desirable that the disposable syringe be pre-filled so that it is not necessary to transfer the injectable solution from a separate ampoule prior to use.

An example of a pre-filled disposable syringe is described in Austrailian patent application 11603/88 in the name of the Applicant. This syringe is sealed at one end (remote form the stopper) by an integral closure which is adapted to be removed so to thereby reveal a needle fitting for the connection of an appropriate hyperdermic syringe and the contents of the syringe for injection.

Whilst the syringe described in Australian patent application 11603/88 is, by and large, a significant improvement over prior prefilled disposable syringes (and these advantages are described therein) it does still present some inconvenience in operation. In particular, the syringe described in this earlier specification requires two distinct and separate operations by the user before the syringe is available for use, namely:

(a) the removal of the closure; and (b) placement of a hyperdermic needle into position onto the revealed needling fitting.

SUMMARY OF THE INVENTION

It is an object of the present invention to provide a disposable pre-filled syringe which is easy to use and which overcomes some of the shortcomings of earlier disposable syringe systems.

According to the present invention, there is provided a pre-filled disposable plastics syringe comprising an open ended barrel having a needle fitting disposed at one end and being sealed at the other end of the barrel by a movable stopper wherein said needle fitting end of the barrel is sealed by a frangible closure which is integral with the needle fitting, said closure being adapted to co-operate with a hyperdermic needle support shaped to fit onto said needle fitting such that application of a downward force on said hyperdermic needle support onto said needle fitting causes said closure to separate from the needle fitting and move at least some way into the body of the syringe and thereby reveal the contents of the syringe for injection.

Preferably, the closure is in the form of a stem having a diameter approximately equal to or smaller than the smallest internal diameter of the needle fitting. It will be apparent to those skilled in the art that the frangible connection of the closure to the needle fitting can be positioned in a number of convenient locations. In one embodiment, this connection is located at the very end of the needle fitting. In the most preferred embodiment of the invention, the point of connection is located a small distance within the needle fitting. This position is preferred because it results in part of the closure member being located within the syringe prior to the application of any separating force. The top end of the needle fitting thereby acts as a guide ensuring that the closure member cleanly enters the body of the syringe upon the application of the separating force.

The closure is preferably of smaller cross section than the needle fitting opening and connected to the internal wall of the needle fitting by a circumferential web. Once this web tears, the closure is of appropriate size to readily move down inside the body of the syringe.

The body of the syringe can be seen as comprising two separate internal compartments. The first being immediately inside the needle fitting section of the syringe body ("the needle fitting compartment") and the second being the remaining section sealed by the stopper at the other end of the syringe body ("the main body compartment"). From a user-confidence perspective it is perceived by the applicant that it would be undesirable for the closure once separated from the needle fitting to drop right down into the main body compartment as it would be seen drifting about in the injectable solution. There would of course be no functional or medical difficulty in this regard as the closure could be fully sterilised. However, to avoid the closure falling into the main body compartment, it is desirable that the internal wall of the needle fitting comprise a stop member that prevents the movement of the closure through to the main body compartment. The stop member can be of any convenient shape which acts as a barrier to the further travel of, the closure but is desirably in the shape of a peripheral shoulder which reduces the internal diameter of the needle fitting to a size smaller than the end of the closure.

As the closure may be forced back up towards its original pre-separated position upon the expression of the injectable solution, in a preferred form of the invention the closure is provided with liquid access means. The means should allow access of liquid past the closure even if it is pressed up immediately adjacent the hyperdermic needle inlet aperture. It will be appreciated that such means may be provided by use of any of a number of different profiles including, corrugations, spiral channels or some other form of channelling. In a preferred embodiment, the liquid access means is provided by a plurality of longitudinally extending channels extending along the full length of the closure. Most preferably, the end of the closure has an internal recess which in conjunction with the longitudinal channels ensures that the hyperdermic needle inlet apperature is not blocked.

The needle fitting moulded into the end of the syringe body can be of any desired form. It is preferably a standard form such as a screw thread fitting or a luer lock fitting.

The syringe body is also preferably moulded with an integral handle in any of the profiles well known in the art. An overcap may also be provided to protect the closure from damage which could cause premature opening of the syringe.

In use, a plunger rod is connected to the end of the stopper located in the open end of the syringe barrel. A hyperdermic needle and support are then placed in position over the top of the closure and onto the top of the needle fitting. The hyperdermic needle itself is also normally provided with an overcap to reduce the risk of injury whilst the needle is being fitted to the syringe. The hyperdermic needle support is then pushed down onto the needle fitting causing the closure to separate from the needle fitting and thereby reveal the contents of the syringe for injection. If a hyperdermic needle overcap is provided, this is then removed and the syringe is ready for use.

BRIEF DESCRIPTION OF THE DRAWINGS

A preferred embodiment of the invention is described in detail hereunder by reference to the accompanying drawings in which:

FIG. 2 is a cross-sectional view of the syringe shown in FIG. 1;

FIG. 3 is an exploded view of the needle fitting of the syringe shown in FIG. 2 with a hyperdermic needle placed adjacent the said needle fitting;

FIG. 4 is a top plan view of the needle fitting closure;

FIG. 5 is a cross-sectional view of a syringe made in accordance with the invention with the hyperdermic needle in position and the closure separated from the needle fitting; and FIG. 6 is an exploded view of the needle fitting and hyperdermic needle as shown in FIG. 5.

DETAILED DESCRIPTION

Figure 1:
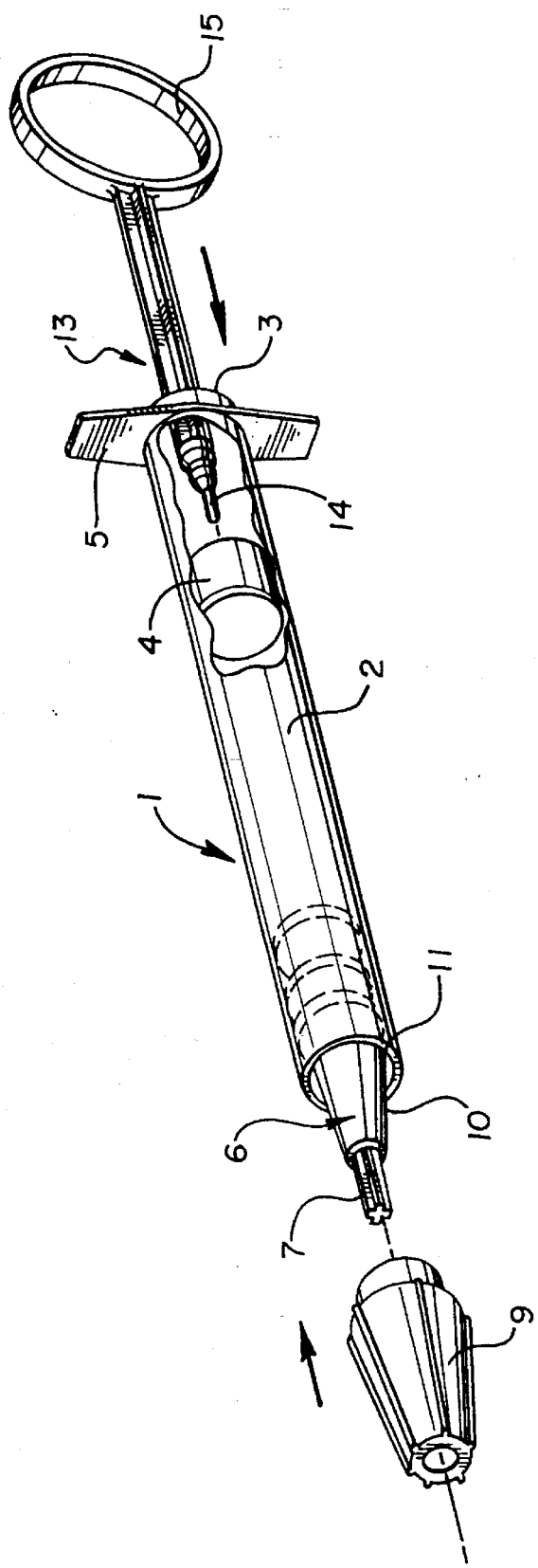
FIG. 1 is a perspective view of a disposable syringe made in accordance with the invention with a plunger rod placed within the syringe body.

In FIG. 1 there is illustrated a pre-filled disposable syringe generally designated by the numeral 1. Syringe 1 comprises an open ended barrel 2 which is sealed at open end 3 by stopper 4. A handle 5 is conveniently provided at the end of barrel 2. A needle fitting 6 is located at the other end of the barrel 2 and comprises an integral closure 7 which is connected to the inside wall 8 of needle fitting 6 (see FIG. 2). Closure 7 and needle fitting 6 are protected by overcap 9 which is shaped to fit over the closure 7 and around the needle fitting 6. Needle fitting 6 is in the form of a standard luer lock comprising a luer cone 10 and an outer wall 11 comprising a screw thread 12 about its inner peripheral wall. Plunger 13 is adapted to co-operate with movable stopper 4 to enable the injectable solution contained within barrel 2 to be expressed once closure 7 is separated from needle fitting inside wall 8. Plunger 13 comprises stopper engaging means 14 and a plunger grip 15.

FIGS. 2 and 3 illustrate cross-sectional details of the needle fitting 6 and associated closure 7. In particular, it will be noted that the closure 7 is connected to the inside wall 8 of needle fitting 6 by peripheral web 16. Closure 7 extends below peripheral web 16 and comprises a base 17 provided with a sloping base wall 18.

Needle fitting 6, as illustrated in FIG. 2, is in the form of a luer lock needle fitting which comprises a luer cone 10 and an outer circumferential wall 11. The outer circumferential wall 11 includes a screw thread 12 positioned about the inner face of this wall. A stopping means is provided by shoulder 19 positioned approximately midway along the length of inside wall 8 of needle fitting 6.

In FIG. 3, there is illustrated the needle fitting of FIG. 2 with a hyperdermic needle 20 and hyperdermic needle support 21 placed generally in position over the top of closure 7 and needle fitting 6. FIG. 3 provides further detail of closure 7. Liquid access means is provided by a plurality of longitudinal channels 22 and recess 23 located at the top of closure 7. A top plan view of closure 7 is shown in FIG. 4.

In use, hyperdermic needle support 21 is pushed down onto the luer cone 10 of needle fitting 6. Before the hyperdermic needle 20 and hyperdermic needle support 21 can be pushed firmly into position, it is necessary to rupture connecting web 16 and thus separate closure 7 from inside wall 8 of needle fitting 6. FIGS. 5 and 6 illustrate this embodiment of the invention following the separation of the closure from inner wall 8 with hyperdermic needle support 21 placed firmly in position over needle fitting 6. Closure 7 is prevented from falling into the main, body compartment 24 due to shoulder 21 interfering with the sloping base wall 18 of closure 7. This is illustrated in detail in FIG. 5. Once the hyperdermic needle and support 23 are placed firmly onto needle fitting 6 as illustrated in FIG. 5, the disposable syringe is immediately available for use. The application of an inward force on plunger 13 causes expression of the injectable fluid housed within syringe barrel 2 through the end 27 of needle fitting 6 and through hyperdermic needle 22. Recess 23 and channels 22 ensure access of the injectable liquid to hyperdermic needle inlet apperature 26. This is well illustrated in FIG. 6 where the top of closure 7 is located immediately adjacent to hyperdermic needle inlet aperture 26.

It will be appreciated that the present invention provides a significant departure from the prior art which leads to simpler and safer operation of the disposable syringe. In use, there is no need to separate the closure from the end of the syringe as a separate step. The placement of the needle support onto the needle fitting is a single operation and once the needle fitting is pressed firmly into position, the syringe assembly is available for immediate use. The disposable syringe assembly of this invention is preferably injection moulded in an aseptic environment. It is preferably manufactured from a thermoplastics material such as polypropylene but may be made of any rigid plastics material. For example, translucent or transparent plastics such as PET, polyamide or TPX may be used. Other suitable materials are well known to those skilled in the art.

It is to be understood that various modifications, additions and/or alterations may be made to the parts previously described without departing from the spirit or ambit of the present invention as defined in the following claims.

I claim:

1. A prefilled disposable plastic syringe comprising an open ended barrel having needle fitting disposed at one end and being sealed at the other end by a moveable stopper, said needle fitting end of the barrel being sealed by a closure which is integral with the needle fitting, said closure being fragibly connected to said needle fitting by a circumferential web such that application of a downward force onto said needle fitting closure will cause said closure to separate from the needle fitting and move at least some way into the syringe to reveal the contents of the syringe for injection.

2. The prefilled disposable plastic syringe as claimed in claim 1 wherein the closure is in the form of a stem having a diameter substantially equal to or smaller than the smallest internal diameter of the needle fitting.

3. The prefilled disposable plastic syringe of claim 1 wherein the closure includes liquid access means; said means permitting access of liquid past the closure after it has been separated from the needle fitting so to enable expression of injectable solution past said closure once separated and out of said plastic syringe.

4. The prefilled disposable plastic syringe as claimed in claim 3 wherein said liquid access means consists of channelling in the surface of the closure.

5. The prefilled disposable plastic syringe as claimed in claim 4 wherein said liquid access means consists of a plurality of longitudinally extending channels.

6. The prefilled disposable plastic syringe as claimed in claim 5 wherein said longitudinally extending channels extend along the full length of the closure.

7. The prefilled disposable plastic syringe of claim 3 wherein the end of the closure comprises an internal recess.

8. The prefilled disposable plastic syringe of claim 1 wherein the closure is frangibly connected to the inside wall of the needle fitting.

9. The prefilled disposable plastic syringe of claim 8 wherein at least part of the closure is located within the needle fitting.

10. The prefilled disposable plastic syringe of claim 1 wherein the body of the syringe comprises a needle fitting compartment located inside the needle fitting section of the syringe body and a main body compartment located in the remaining portion of the syringe body which is sealed by the moveable stopper wherein a portion of the internal wall of the needle fitting comprises a stop member that prevents movement of the closure into the main body compartment of the syringe after it has been separated from the needle fitting.

11. The prefilled disposable plastic syringe as claimed in claim 10 wherein said stop member is formed by a peripheral shoulder which is located on the internal wall of the needle fitting which reduces the internal diameter of the needle fitting to a size smaller than the end of the closure.

12. The prefilled disposable plastic syringe of claim 1 wherein the needle fitting is in the form of a leur lock needle fitting.

13. A prefilled disposable plastic syringe comprising an open ended barrel having a needle fitting disposed at one end and being sealed at the other end by a moveable stopper, said needle fitting end of the barrel is sealed by a closure which is integral with the needle fitting, said closure being frangibly connected to said needle fitting such that application of a downward force onto said needle fitting closure will cause said closure to separate from the needle fitting and move at least some way into the syringe to reveal the contents of the syringe for injection, wherein the body of the syringe comprises a needle fitting compartment located inside the needle fitting section of the syringe body and a main body compartment located in the remaining portion of the syringe body which is sealed by the moveable stopper wherein a portion of the internal wall of the needle fitting comprises a stop member that prevents movement of the closure into the main body compartment of the syringe after it has been separated from the needle fitting.

14. The prefilled disposable plastic syringe as claimed in claim 13 wherein said stop member is formed by a peripheral shoulder which is located on the internal wall of the needle fitting which reduces the internal diameter of the needle fitting to a size smaller than the end of the closure.

* * * * *

UNITED STATES PATENT AND TRADEMARK OFFICE
CERTIFICATE OF CORRECTION

PATENT NO. : 5,478,321
DATED : December 26, 1995
INVENTOR(S) : Michael B. Kimber It is certified that error appears in the above-indentified patent and that said Letters Patent is hereby corrected as shown below:

Column 4, line 47, delete "fragibly" and insert -- frangibly -- .

Signed and Sealed this

Sixteenth Day of April, 1996

Attest:

BRUCE LEHMAN

Attesting Officer

Commissioner of Patents and Trademarks